United States Patent [19]

Pouletty

[11] Patent Number: 5,223,397
[45] Date of Patent: Jun. 29, 1993

[54] SOLUBLE HLA CROSS-MATCH

[75] Inventor: Philippe Pouletty, Atherton, Calif.

[73] Assignee: Sangstat Medical Corporation, Menlo Park, Calif.

[21] Appl. No.: 710,710

[22] Filed: Jun. 5, 1991

[51] Int. Cl.$^5$ ............... G01N 33/543; G01N 33/564; G01N 33/566

[52] U.S. Cl. .................. 435/7.24; 435/7.8; 435/7.95; 436/501; 436/507; 436/518

[58] Field of Search .......... 435/7.24, 7.94, 7.95, 435/7.8; 436/518, 501, 507

[56] References Cited

U.S. PATENT DOCUMENTS

| | | | |
|---|---|---|---|
| 4,810,632 | 3/1989 | McMillan | 435/7 |
| 4,891,319 | 1/1990 | Roser | 435/188 |
| 4,895,706 | 1/1990 | Root et al. | 422/102 |
| 4,959,308 | 9/1990 | Ogden | 435/7 |

OTHER PUBLICATIONS

P. Tijssen *Practice and Theory of Enzyme Immunoassays*, Elsevier Science Publishers B.V., Amsterdam, 1985, pp. 330 and 341.

Duquesnay et al., *Transplantation*, (1990), 50:427-37. Title: Multiscreen serum analysis of highly sensitized renal dialysis patients for antibodies toward public and private class I HLA determinants. Implication for computer-predicted acceptable and unacceptable donor mismatches in kidney transplantation.

Martin et al., *Transplantation*, (1987), 44:50-53. Title: Posttransplant antidonor lymphocytotoxic antibody production in relation to graft outcome.

Grosse-Wilde et al., *J. Immunogenet.* (1989), 16:149-55. Title: Allotyping for HLA class I using plasma as antigen source.

Doxiadis et al., *Blut (West Germany)*, (1989), 59:449-54. Title: Quantification of soluble HLA class I gene products by an enzyme linked immunosorbent assay.

Doxiadis and Grosse-Wilde, *Vox Sang.* (1989), 56:196-9. Title: Typing for HLA class I gene products using plasma as source.

Davies et al., *Transplantation*, (1989), 47:524-527. Title: Soluble HLA antigens in the circulation of liver graft recipients.

Tsuji et al., *Tokai J. Exp. Clin. Med.*, (1985), 10:169-74. Title: Biological significance of Ss (serum soluble) HLA-class I antigens in bone marrow transplantation.

Stevenson et al., *J. Immunol. Methods*, (1986), 86:187-90. Title: Analysis of soluble HLA class II antigenic material in patients with immunological diseases using monoclonal antibodies.

Fauchet et al., *Transplantation*, (1989), 30:114-129. Title: Occurrence and Specificity of Anti-B Lymphocyte Antibodies in Renal Allograft Recipients.

Talbot et al., *J. Immunol. Methods*, (1988), 112: 279-83. Title: Rapid detection of low levels of donor specific IgG by flow cytometry with single and dual colour fluorescence in renal transplantation.

Iwaki et al., *Clin. Transplantation*, (1988), 2:81-4. Title: Successful transplants across warm-positive crossmatches due to IgM antibodies.

*Primary Examiner*—David Saunders
*Attorney, Agent, or Firm*—Bertram I. Rowland

[57] ABSTRACT

Soluble HLA cross-matches are determined by providing for antibodies or ligand bound to a solid substrate specific for at least one HLA allele and detecting complexes between either donor or recipient HLA antigens and recipient or donor antibodies, respectively, or reference HLA and patient antibodies, particularly IgG antibodies. Conveniently, anti-human immunoglobulin (Ig), particularly human IgG, conjugates are employed where the anti-human Ig is conjugated with a label capable of providing a detectable signal to permit detection of human anti-HLA bound to said solid substrate.

14 Claims, No Drawings

SOLUBLE HLA CROSS-MATCH

TECHNICAL FIELD

The field of this invention is the detection of HLA reactive antibodies.

BACKGROUND

In many situations, there is concern for differences between the HLA type of a cell source and the cell recipient. In situations where allogeneic cells or tissue are taken from a donor and introduced into a recipient, it is desirable that the donor and recipient be as closely HLA matched as possible The presence in the patient serum of antibodies against HLA antigens of the donor (donor specific crossmatch) or against a high percentage of HLA alleles (PRA testing) predicts a high risk of graft rejection.

The standard technique is microcytotoxicity, where patient serum is incubated with donor or panel lymphocytes, then with complement; the level of cytotoxicity is then estimated by discriminating between dead and viable cells using a dye. This method has numerous disadvantages: it is labor intensive; time consuming; requires isolation of cells; requires viable cells; is non-specific; and requires a subjective evaluation. In addition, the methodology does not discriminate between IgG and IgM, where it is believed that IgM does not have a negative prognosis value as compared with IgG. Flow cytometry may also be used but requires cells and expensive instrumentation.

It is therefore of interest to provide alternative techniques which can be performed simply, can be automated, do not share the shortcomings described above, and provide a readily discernible result which is significant for the prognosis of graft acceptance.

Relevant Literature

References of interest include Duquesnoy et al., (1990) Tranplantation 50: 427-37; Martin et al. (1987) 44: 50-53; Grosse-Wilde et al. (1989) J. Immunogenet. 16: 149-55; Doxiadis et al. (1969) 59: 449-54; Doxiades and Grosse-Walde (1989) Vox Sang 56: 196-9, Davies et al. (1989) Transplantation 47: 524-7; Tsuji et al. (1985) Tokai J. Exp. Clin. Med. 10: 169-74; Stevenson et al. (1986) J. Immunol. Methods 86: 187-90; Fauchet et al. (1989) Transplantation 30: 114-129; Talbot et al. (1988) J. Immunol. Methods 112: 279-83; Iwaki et al. (1988) Clin. Tranplantation 2:81-4.0

SUMMARY OF THE INVENTION

HLA cross-matching is performed by combining blood, serum or plasma, from a tissue or cell donor or tissue culture supernatant from a lymphoblastoid transfected cell line with antibodies or ligand specific for HLA molecules, so as to bind soluble HLA molecules to a solid substrate. Blood, serum or plasma from the recipient is then added to allow antibodies specific for the bound HLA to bind. Human antibodies which become bound to the solid substrate through the binding to the HLA molecules are then detected by any convenient means as indicative of an undesirable cross-match. Alternatively, one may rely on immune complexes for the antibody and soluble HLA or the order of combination may be varied.

The cross-match can also be done against a panel of human serum specimens of known HLA phenotype using the same method to estimate the level of sensitization against various phenotypes.

DESCRIPTION OF THE SPECIFIC EMBODIMENTS

In accordance with the subject invention antibodies of a graft recipient for HLA molecules of the donor are detected using anti-hIg antibodies under conditions which allow for detection of the recipient's IgG antibodies against donor soluble HLA molecules or the reverse in the case of bone marrow transplants (graft-versus-host disease). Usually, by combining serum or plasma from a cell (includes tissue) donor and sequestering the complex to a solid substrate, the presence of the complex is then determined.

In the preferred embodiment, antibodies against HLA antigens are provided bound to a solid substrate (capture antibodies). The substrate-bound-antibodies are combined with blood or derivative thereof, serum or plasma (hereafter "blood") from a cell donor. After sufficient time for soluble HLA molecules to bind, blood from the recipient is added to the bound HLA molecules and incubated for sufficient time for any antibodies to bind. The presence of such human antibodies bound to the HLA molecules is then determined. Alternatives protocols include incubating soluble HLA with recipient blood and then capture antibodies or having a single incubation of the three components. The order of addition of the components is not critical, but the first indicated protocol is preferred. The level of antibodies in the recipient blood is indicative of the degree of immune sensitization and the likelihood of acceptance of the allogeneic cells.

In carrying out the method, one prepares ligand or antibodies bound to a solid substrate which are specific for all or a subset of HLA molecules, where such HLA molecules include Class I and Class II, A, B, C, DR, DP or DQ or may be group or allele specific, such as A2, DRw2, or DR4, etc. The particular choice of antibodies will depend upon what is known about the donor and recipient and which HLA molecules are believed to be of concern. The antibodies may be from any source, preferably from a source other than human, where a human cross-match is being measured. In that way, one can be reasonably assured that the labeled molecules for binding to the antibodies will not also bind to the antibodies bound to the surface. Alternatively, one may use a class or isotype to which the labeled molecules will not bind. Instead of whole or intact antibodies, one may use antibody fragments, e.g., F(ab')$_2$ or other peptides or proteins which have an affinity to HLA, e.g., CD8 surface membrane protein receptors, etc.

The antibodies may be bound to the surface by any convenient means, depending upon the nature of the surface. The surface may be a solid surface, porous surface, may be made of glass, plastic, e.g., polystyrene, nitrocellulose or the like. The antibodies may be bound covalently or non-covalently by conventional techniques. The particular manner of binding the antibodies is not crucial to this invention and any convenient technique which allows for the availability of the binding sites may be employed. Preferably, a porous surface is used, which will allow for the passage of fluids during the assay.

The antibodies may be specific for a-heavy chain for the Class I HLA molecules, A, B or C, or the $\beta_2$-microglobulin chain or an epitope expressed by a subset of HLA molecules resulting from alternative splicing or polymerization or the α or β- chain for Class II HLA molecules. As indicated, the antibodies or other binding molecule may be directed to a constant region or a portion of the variable region of specific alleles.

The amount of antibody which is bound will be sufficient to ensure that sufficient amount of soluble HLA is bound, so as to be able to detect the presence of the cross-match.

In order to ensure that non-specific binding is minimized, usually the surface will be coated with an innocuous protein and/or detergent to inactivate hot spots. Various proteins may be used, such as bovine serum albumin, casein and the like. Detergents include Tween, SDS, and the like. By incubating the antibody coated surface with a buffered solution of the protein, the amount of non-specific binding may be substantially reduced.

The particular surface which is employed may be microtiter plates, where the bottom may be solid or porous, filters, slides, tubes, or the like. Most conveniently are microtiter plates, where a large number of assays may be carried out simultaneously, using small amounts of reagents and samples.

The sample containing the soluble HLA may then be added to the bound antibody, the sample usually being serum or plasma, with or without prior dilution. Dilution will generally be with an appropriate buffered medium, e.g. 0.1M PBS at pH 7-8. The incubation time should be sufficient to allow for binding of soluble HLA molecules to the substrate bound antibody. Generally from about 0.15 to 3 h is sufficient, usually 1 h sufficing. The volume of the sample which is added is sufficient to allow for substantial binding of HLA molecules to the surface. After the incubation, the surface may be washed, particularly with a dilute non-ionic detergent medium at an appropriate pH, generally 7-8, to remove non-specific binding protein. From one to five washes may be employed, with sufficient volume to thoroughly wash non-specifically bound proteins present in the sample. By serum or plasma is intended a blood sample free of erythrocytes and frequently substantially free of white blood cells.

The recipient's blood sample is then added to the bound HLA molecules. Conveniently, the recipient sample may be diluted from about 1:1 to 1:500, preferably about 1:10 or titered to determine the endpoint, in an appropriate buffered medium, e.g. 0.05-0.2M PBS, pH 7-8, desirably containing an innocuous protein in from about 0.5-2% w/v. Incubation may then be carried out for sufficient time for binding to occur, usually at least about 0.15 h and not more than about 3 h, generally 1 h sufficing. After the recipient sample has been incubated for sufficient time to ensure binding to have occurred, the surface may then be washed, as described above, to remove any non-specific binding antibodies.

Alternative protocols may be employed, which will depend, in part, on whether the sample from the recipient is prior or subsequent to the transplant. When subsequent, one can bind any immune complexes present in the sample to the substrate-bound-anti-HLA, without having to add blood from the donor, followed by blood from the recipient. As already indicated, instead of using blood from the donor to supply the HLA, one may use blood of known HLA phenotype which may be bound to a solid substrate by filtration, antibodies or other means. A panel of serum specimens containing HLA of known phenotype is employed. The shorthand acronym "PRA" indicates a "panel of reactive lymphocytotoxic antibodies." The PRA is a screen of patient sensitivity. See Duquesnoy, et al. (1990), supra. Usually the panel will range from 20 to 40 specimens, which specimens are representations of the population. The higher the percentage of reactivity, the higher the level of sensitization. The assay may then be carried out in the same manner as for the soluble HLA and substrate-bound-anti-HLA or capture antibodies.

It may be desirable to reduce or remove soluble HLA from the recipient blood serum or plasma, specimen prior to testing. Affinity chemotography for one or more epitopes, magnetic beads, or other specific separation means may be employed. The separation and removal of the recipient HLA will increase sensitivity by avoiding competition between HLA bound to the capture antibodies and HLA in the recipient specimen. Rates of complex formation may be enhanced by membrane flow-through, heating, sonication, precipitating agents, and the like.

The sample is now ready to be assayed by combining the substrate with anti-human Ig conjugate, any isotype, particularly IgG, where the conjugate carries a label which provides for detection. The anti-human Ig antibody will be at a concentration usually sufficient for binding all of the human antibody which has become bound to the substrate. Generally, the conjugate is commercially available and may be diluted as obtained at least about 1:10, usually about 1:100 and up to about 1:3000, usually about 1:500. Conveniently, the conjugate may be diluted in a buffered solution at physiologic pH, usually in the range of about 6.8 to 9.5, preferably about 7.4, where the buffer is conveniently PBS at about 0.05 to 0.2 M, preferably 0.1 M. The solution may also contain an innocuous protein as described previously, in the same concentration range. Usually, incubation will be carried out for at least about 15 min, more usually at least about 0.5 h, and not more than about 3 h, preferably about 1 h. In a microtiter well, conveniently about 100 μL of the conjugate will suffice.

The anti-Ig will usually come from any source other than human, such as ovine, rodentia, particularly mouse, bovine, etc. The particular source is not significant. Any convenient label may be used, which allows for detection at the concentration range of interest. Also, the choice of the label may vary, whether visual detection is employed or a device, such as a spectrophotometer or fluorimeter. Labels may therefore include enzymes, where the substrate may provide for a colored or fluorescent product, radioisotopes, fluorescers, dyes, beads, chemiluminescers, colloidal particles, and the like. The particular label is not critical to this invention, so long as it provides the desired signal and sensitivity.

After sufficient time for the conjugate to bind to any human Ig present on the substrate, usually less than about 1 h, and washing to remove non-specifically bound conjugate, the signal may be detected in accordance with conventional ways. Where an antibody is employed, the leuco dye or fluorescer precursor will be added under conditions where the colored or fluorescent product will be produced. Desirably, a dye may be used which forms a soluble or insoluble product, which is intensely colored or black. A convenient pair is the use of peroxidase with ortho-phenylene diamine or TMB. Other enzymes which may find use include alkaline phosphatase, urease, luciferase, or the like. Once the product is formed, it may be detected visually or by means of an instrument. If a quantitative determination is desirable, the concentration of specific antibodies may be estimated by endpoint titration of the test specimen or by comparison of the optical density or other signal with standard specimens.

A device which may find application with the subject invention is one having a porous substrate to which the antibody specific for the HLA is bound. Supporting the substrate is an absorbent layer which will absorb the various fluids, including samples and washes. Desirably, the absorbent layer and porous layer are separated by a flow control film, having a plurality of orifices which direct the rate and direction of flow through the porous layer. For further description of this device, see U.S. application serial no. 444,814, filed Dec. 1, 1989 and now abandoned. This device, as well as comparable devices allow for the simultaneous determination of a plurality of samples and a plurality of HLA antigens, either from different sources, or at different concentrations from the same source. Thus, one can carry out a plurality of determinations at the same time. Alternatively, microtiter plate wells may be employed, where the bottoms of the wells are porous to allow for filtration or the bottoms are solid requiring repetitive washing to remove fluid from each of the wells. The particular device which is employed will depend upon the number of samples to be determined, available equipment, and the like.

The following examples are offered by way of illustration and not by way of limitation.

EXPERIMENTAL

A microtiter plate (Nunc) is coated with an anti-β-2-microglobulin monoclonal antibody (coating 1 h at 37° C. with 1 μg/ml antibody in 0.1 M PBS pH 7.4, 100 μL per well, followed by blocking with 0.1 M PBS pH 7.4 containing 1% casein w/v); target serum is incubated for 1 h, 100 μL per well at room temperature. After washing 3×with 250 μL per well of PBS with 0.1% Tween −20, diluted test serum (100 μL/well of a 1:10 dilution in 0.1 M PBS pH 7.4 containing 1% casein w/v) is incubated for 1 h at room temperature. After washing as above, an anti-human IgG goat antibody-peroxidase conjugate (Jackson Laboratories), diluted 1:500 in 0.1M PBS pH 7.4 containing 1% casein w/v is added (100 μL per well for 1 h). After washing as above, ortho-phenyl-ene diamine (10 mg/ml in citrate phosphate buffer pH 5 with hydrogen peroxide) is added (100 μL per well) and incubated in the dark for 15 min. Colored development, optical density (O.D.) is measured using a spectrophotometer at 495 nm.

The concentration of specific antibodies can be estimated by endpoint titration of the test specimen or by comparison of the O.D. with standard specimens.

The subject method provides substantial improvements over what has been previously available. The subject method is easy to use, rapid, and does not require cells. The subject method is adaptable, so that it can be HLA (class, locus or allele) specific. In addition, one can be isotype specific for the antibody, namely IgG or such other antibody as may be of interest. The method can be used before transplantation and be used for graft rejection monitoring after transplantation. It avoids many of the pitfalls of the presently available method in its simplicity, rapidity, lack of requirement for cells, and objective determination.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for testing HLA compatibility between two humans, a donor and a recipient, said method comprising:
    adding blood from the donor to a substrate to which antibodies or ligand to at least one HLA allele are bound and incubating for sufficient time for soluble HLA antigens present in said blood to bind to said antibodies or ligand;
    adding blood from said recipient to said solid substrate, whereby any antibody specific for any HLA antigens bound to said solid substrate may become bound; and
    detecting the absence of antibodies from recipient blood to said HLA antigen as indicative of a crossmatch.

2. A method according to claim 1, wherein said antibodies or ligand to said HLA antigen allele bind to antigens of Class I HLA antigens.

3. A method according to claim 1, wherein said detection is by means of an anti-Ig labeled conjugate.

4. A method according to claim 3, wherein anti-Ig is anti-IgG.

5. A method according to claim 3, wherein said label is an enzyme.

6. A method according to claim 1, wherein said antibodies or ligand to at least one HLA allele are bound to a porous solid substrate.

7. A method for detecting anti-HLA antibodies in an explant recipient who has received or is to receive said explant from a d determine the likelihood of a successful explant, said method comprising:
    combining blood from said donor and recipient with a solid substrate which antibodies are bound to at least one HLA allele and incubating for sufficient time for complexes of HLA antigens and anti-HLA antibodies to bind to said antibodies to at least one HLA allele; and
    detecting said anti-HLA antibodies of said complex.

8. A method according to claim 7, wherein said explant is bone marrow, kidney, liver or heart.

9. A method according to claim 7, wherein said solid substrate is porous.

10. A method according to claim 7, wherein said detecting is by means of a labeled anti-human Ig conjugate, wherein said label provides a detectable signal.

11. A method for detecting human anti-HLA antibodies in a human transplant patient, wherein said detection occurs either before or after transplantation, said method comprising:
    incubating a liquid specimen containing soluble human HLA antigens, said soluble HLA antigens being from a human donor blood specimen, a human cell line culture supernatant or from blood of said human transplant patient, with a solid substrate to which a plurality of other than human antibodies are bound, said plurality of other than human antibodies being specific for one or more human HLA alleles said incubating being for sufficient time for said human soluble HLA antigens to bind to other than human antibodies, said human soluble HLA antigens being uncomplexed with human anti-HLA antibodies when from said human donor blood or supernatant or being complexed with human anti-HLA antibodies when from blood of said human transplant patient;

wherein when said liquid specimen is from human donor blood or supernatant, providing the additional step of incubating the solid substrate and any human soluble HLA antigen bound to said solid substrate with blood from said human transplant patient; and detecting the presence of human anti-HLA antibodies to said soluble HLA antigens bound to said solid substrate.

12. A method according to claim 11, wherein said explant is bone marrow, kidney, liver or heart.

13. A method according to claim 11, wherein said solid substrate is porous.

14. A method according to claim 13, including the additional steps of washing after each adding and withdrawing said washes through said porous solid substrate.

* * * * *